US009944599B2

(12) United States Patent
Stavber et al.

(10) Patent No.: US 9,944,599 B2
(45) Date of Patent: Apr. 17, 2018

(54) PROCESSES FOR THE PREPARATION OF BETA-AMINOSULFONE COMPOUNDS

(71) Applicant: Lek Pharmaceuticals d.d., Ljubljana (SI)

(72) Inventors: Gaj Stavber, Ljubljana (SI); Jerome Cluzeau, Ljubljana (SI)

(*) Notice: Subject to any disclaimer, the term of this patent is extended or adjusted under 35 U.S.C. 154(b) by 0 days.

(21) Appl. No.: 15/322,303

(22) PCT Filed: May 27, 2015

(86) PCT No.: PCT/EP2015/061744
§ 371 (c)(1),
(2) Date: Dec. 27, 2016

(87) PCT Pub. No.: WO2015/181249
PCT Pub. Date: Dec. 3, 2015

(65) Prior Publication Data
US 2017/0174627 A1 Jun. 22, 2017

(30) Foreign Application Priority Data
May 28, 2014 (EP) .................................. 14170338

(51) Int. Cl.
C07D 209/48 (2006.01)
C07C 315/04 (2006.01)
C07C 319/18 (2006.01)
C07C 315/02 (2006.01)

(52) U.S. Cl.
CPC .......... *C07D 209/48* (2013.01); *C07C 315/02* (2013.01); *C07C 315/04* (2013.01); *C07C 319/18* (2013.01)

(58) Field of Classification Search
CPC ............................ C07C 315/02; C07D 209/48
See application file for complete search history.

(56) References Cited

U.S. PATENT DOCUMENTS

| 8,981,117 B2* | 3/2015 | Connolly | ............. | C07D 209/48 548/472 |
| 9,126,906 B2* | 9/2015 | Connolly | ................ | C07B 53/00 |
| 9,434,689 B2* | 9/2016 | Connolly | ............. | C07D 209/48 |
| 2013/0131180 A1 | 5/2013 | Kawai et al. | | |
| 2013/0345126 A1 | 12/2013 | Boehme et al. | | |

FOREIGN PATENT DOCUMENTS

| WO | 0025777 | 5/2000 |
| WO | 03080049 A1 | 10/2003 |
| WO | 2010030345 A2 | 3/2010 |
| WO | 2013126360 A2 | 8/2013 |
| WO | 2013126495 A2 | 8/2013 |

OTHER PUBLICATIONS

PCT International Search Report and Written Opinion for PCT/EP2015/061744, dated Jul. 24, 2015, 13 pages.
Barlow, Kenneth N., et al., Elimination and Addition Reactions. Part 33. Formation and Behavior of Carbanions Derived from Sulphones and Nitriles bearing Beta-Onium Substituents, Journal of the Chemical Society, Jan. 1, 1977, p. 1920.
Favier, Isabelle, et al., CoCl2 catalysed decarboxylation-oxidation of mandelic acids by molecular oxygen, New Journal of Chemistry, Jan. 1, 2004, p. 62.
Meciarova, Maria, et al., Study of SnAr Reactions of Halobenzenes with Imidazole under Ultrasonic and Microwave Irradiation, Monathefte Fur Chemie, vol. 135, 2004, pp. 419-423.
Meyle, Eberhard, et al., Darstellung und Eigenschaften von 2,3-disubstituierten 1,2-Thiazetidin-1, 1-dioxiden, Liebigs Annalen der Chemie, Aug. 2, 20184, pp. 802-812.
Min, Shi, et al., The reactions of DMSO with arylaldehydes in the presence of sodium hydride, J. Chem Research, 2002, pp. 422-427.
Russell, Glen A., et al., Autoxidation and Condensation reactions of carbanions in dimethylsulfoxide solution, Journal of the American Chemical Society, vol. 84, No. 13, Jul. 1, 1962, pp. 2652-2653.
Wang, Fei, et al., Convenient one-step synthesis of cis-2, 4, 5-Triarylimidazolines from Aromatic Aldehydes with Urea, Synthetic Communications, vol. 42, No. 6, Mar. 15, 2012, pp. 905-913.

* cited by examiner

*Primary Examiner* — Golam M Shameem
(74) *Attorney, Agent, or Firm* — Luedeka Neely Group, P.C.

(57) ABSTRACT

The present invention relates to processes for preparing β-aminosulfone compounds. The provided compounds are useful intermediates in the preparation of sulfone group containing isoindoline-based compounds, in particular apremilast.

10 Claims, No Drawings

PROCESSES FOR THE PREPARATION OF BETA-AMINOSULFONE COMPOUNDS

This application is a Section 371 national phase entry of PCT application PCT/EP2015/061744, filed May 27, 2015. This application also claims the benefit of the earlier filing date of European patent application 14170338.9, filed May 28, 2014.

FIELD OF THE INVENTION

The present invention relates to processes for preparing β-aminosulfone compounds. The provided compounds are useful intermediates in the preparation of sulfone group containing isoindoline-based compounds, in particular apremilast.

BACKGROUND OF THE INVENTION

The synthesis of sulfone compounds and in particular β-aminosulfone compounds is of interest because these compounds themselves can have favourable properties and may furthermore be useful in the preparation of compounds with a potential for biological activities. β-Aminosulfones play an important role in physiological processes and are for instance used as intermediates in the synthesis of α-amino acids, amino alcohols, uridines, adenosines, alkaloids, β-lactams, etc.

β-Aminophenethyl sulfone derivatives have shown potential to treat inflammatory diseases, in particular globally relevant inflammatory diseases such as arthritis and related arthritic conditions such as psoriatic arthritis, psoriasis, and Crohn's disease. Specifically, this class of compounds shows promising potential as selective phosphodiesterase 4 (PDE IV or PDE4) type inhibitors.

The synthesis of sulfone compounds and in particular β-aminosulfone compounds may thus provide useful intermediates for the synthesis of anti-inflammatory agents, preferably active for treatment of psoriatic arthritis, and in particular for the synthesis of apremilast. Apremilast, which is N-{2-[(1S)-1-(3-ethoxy-4-methoxyphenyl)-2-(methylsulfonyl)ethyl]-1,3-dioxo-2,3-dihydro-1H-isoindol-4-yl}acetamide, is an inhibitor of PDE4. Apremilast specifically inhibits PDE4 and spontaneous production of TNF-α from human rheumatoid synovial cells and has anti-inflammatory activity.

WO 00/25777 A1 describes the synthesis of the racemate of apremilast and derivatives thereof. WO 03/080049 A1 describes the optical resolution of a racemic β-aminosulfone intermediate using stoichiometric amounts of enantiomerically pure chiral amino acids to obtain apremilast. However, in both cases the overall synthetic routes are lengthy requiring several steps and use expensive as well as hazardous materials. In WO 2010/030345 A2 a synthesis of apremilast is described which inter alia includes the formation of a benzonitrile derivative and furthermore a reduction step.

WO 2013/126360 A2 and WO 2013/126495 A2 describe processes to produce apremilast which include the preparation of enantiomerically pure chiral β-aminosulfone intermediates using expensive as well as toxic materials such as metal catalysts, ligands or chiral auxiliaries.

The object of the present invention is to provide short, simple, cost-effective, environmentally friendly and industrially suitable synthetic processes for preparing β-amino sulfone, sulfoxide and sulfide intermediates useful for the preparation of sulfone group containing isoindoline-based compounds, in particular apremilast.

SUMMARY OF THE INVENTION

The object is solved by the methods, the compound, and the use of the compound described below.

The present invention in particular provides various aspects, advantageous features and preferred embodiments as summarized in the following items, which respectively alone or in combination particularly contribute to solving the object of the invention and eventually provide additional advantages:

(1) A process for preparing a compound of formula (I)

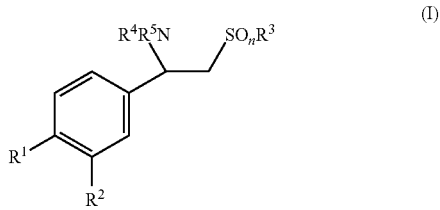

or a salt or solvate thereof, the process comprising the steps of:
(a) providing a compound of formula (II)

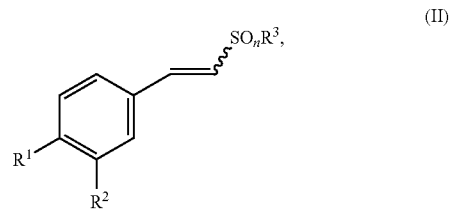

and
(b) contacting the compound of formula (II) with $R^4R^5NH$ or a conjugate base thereof or with $XYC=NH$ in a solvent,
to obtain the compound of formula (I),
wherein $R^1$ and $R^2$ are each independently selected from the group consisting of hydrogen, hydroxy, halogen, nitro, cyano, —$CF_3$, substituted or unsubstituted $C_1$-$C_6$ alkyl, substituted or unsubstituted $C_3$-$C_6$ cycloalkyl, substituted or unsubstituted $C_1$-$C_6$ alkoxy, substituted or unsubstituted $C_3$-$C_6$ cycloalkoxy, substituted or unsubstituted $C_6$-$C_{10}$ aryl, and substituted or unsubstituted $C_7$-$C_{12}$ aralkyl;
$R^3$ represents substituted or unsubstituted $C_1$-$C_6$ alkyl, hydroxy, substituted or unsubstituted $C_6$-$C_{10}$ aryl, substituted or unsubstituted $C_7$-$C_{12}$ aralkyl, or —$NR^6R^7$, wherein $R^6$ and $R^7$ are each independently selected from the group consisting of hydrogen, substituted or unsubstituted $C_1$-$C_6$ alkyl, substituted or unsubstituted $C_6$-$C_{10}$ aryl, and substituted or unsubstituted $C_7$-$C_{12}$ aralkyl;
$R^4$ and $R^5$ are each independently selected from the group consisting of hydrogen, hydroxy, and substituted or unsubstituted $C_1$-$C_4$ alkyl;
X and Y are each independently selected from phenyl and tert-butyl;
n is an integer selected from 0, 1 and 2;

and the wavy line indicates (E)- or (Z)-isomer or a mixture of (E)- and (Z)-isomers.

(2) The process according to item (1), wherein the compound of formula (II) is the (E)-isomer.

(3) The process according to item (1) or (2), wherein the solvent comprises water, preferably the solvent is substantially aqueous, and more preferably the solvent is water.

(4) The process according to any one of the preceding items, wherein the compound of formula (I) is a substantially racemic compound, preferably is the racemic compound.

(5) The process according to any one of the preceding items, wherein step (b) does not comprise a stereoselective addition.

(6) The process according to any one of the preceding items, wherein $R^1$ is methoxy or hydroxy, preferably is methoxy, $R^2$ is ethoxy, and $R^3$ is methyl.

(7) The process according to any one of the preceding items, wherein $R^4$ or $R^5$ represents hydrogen, preferably $R^4$ and $R^5$ each represent hydrogen (8) The process according to any one of the preceding items, wherein the compound of formula (I) is 2-(3-ethoxy-4-methoxyphenyl)-1-(methanesulfonyl)-eth-2-ylamine, having formula (Ia)

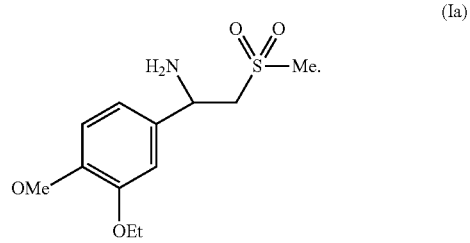 [SMILES: CCOc1cc(C(N)CS(C)(=O)=O)ccc1OC]

(9) The process according to any one of items (1) to (7), wherein the compound of formula (I) is 2-(3-ethoxy-4-methoxyphenyl)-1-(methanesulfinyl)-eth-2-ylamine or 2-(3-ethoxy-4-methoxyphenyl)-1-(methanesulfanyl)-eth-2-ylamine.

(10) The process according to any one of the preceding items, wherein the compound of formula (II) is a compound having formula (IIa)

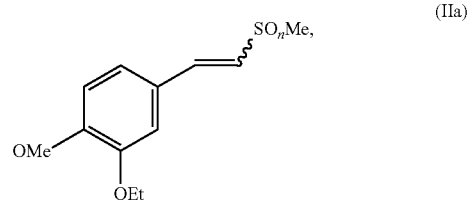

wherein n is an integer selected from 0, 1 and 2, wherein the wavy line is as defined above, and wherein preferably the compound of formula (IIa) is the (E)-isomer.

(11) The process according to any one of the preceding items, wherein step (b) is carried out at a temperature from 25° C. to 135° C., preferably from 50° C. to 110° C., more preferably from 60° C. to 100° C., even more preferably from 80° C. to 100° C., and in particular at around 80° C.

(12) The process according to any one of the preceding items, wherein step (b) is carried out in the presence of a catalyst, preferably an acid catalyst, more preferably boric acid catalyst.

(13) The process according to any one of the preceding items, wherein step (a) comprises:
(i) providing a compound of formula (III)

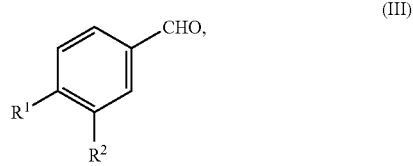

and
(ii) contacting the compound of formula (III) with $R^8SO_mR^9$, optionally in the presence of a base, wherein $R^8$ and $R^9$ each independently correspond to $R^3$, and m is 1 or 2.

(14) The process according to item (13), wherein $R^8$ and $R^9$ each represent methyl.

(15) The process according to item (13) or (14), wherein contacting according to step (ii) is carried out in the presence of a base, more preferably potassium tert-butoxide, KOH, $Et_3N$, $Cs_2CO_3$ or BuLi.

(16) The process according to any one of items (13) to (15), wherein m is 2.

(17) The process according to any one of items (13) to (15), wherein m is 1.

(18) The process according to item (17), wherein after step (ii) formic acid and $H_2O_2$ are added.

(19) The process according to any one of items (13) to (18), wherein $R^1$ is methoxy or hydroxy, and $R^2$ is ethoxy.

(20) The process according to any one of items (13) to (19), wherein the compound of formula (III) is 3-ethoxy-4-methoxy-benzaldehyde, having formula (IIIa)

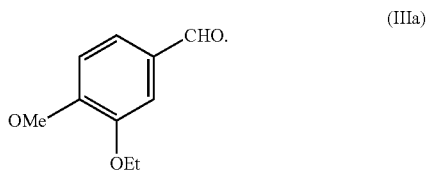 [SMILES: CCOc1cc(C=O)ccc1OC]

(21) A process for preparing apremilast or a pharmaceutically acceptable salt or solvate thereof, comprising:
(aa) carrying out the process according to any one of the preceding items, and
(bb) subsequently carrying out further synthetic step(s) to obtain apremilast.

(22) The process according to item (21), wherein $R^1$ is methoxy or hydroxy, $R^2$ is ethoxy, and $R^3$ is methyl.

(23) The process according to item (21) or (22), wherein $R^4$ or $R^5$ represents hydrogen, preferably $R^4$ and $R^5$ each represent hydrogen.

(24) The process according to any one of items (21) to (23), wherein the procedure in (bb) comprises chiral resolution or chiral enrichment.

(25) The process according to any one of items (21) to (24), wherein $R^1$ is methoxy, and $R^4$ and $R^5$ are each hydrogen.

(26) The process according to any one of items (21) to (25), wherein n as defined in item (1) is 0, 1 or 2, preferably is 1 or 2, more preferably is 2.

(27) A process for preparing a pharmaceutical composition comprising apremilast or a pharmaceutically acceptable salt or solvate thereof, the process comprising the steps of carrying out the process according to any one of items (21) to (26) to obtain apremilast or a pharmaceutically acceptable salt or solvate thereof, and mixing said obtained apremilast or a pharmaceutically acceptable salt or solvate thereof, optionally with another active pharmaceutical ingredient, with a pharmaceutically acceptable excipient, carrier and/or diluent.

(28) A compound having any one of the following formulae:

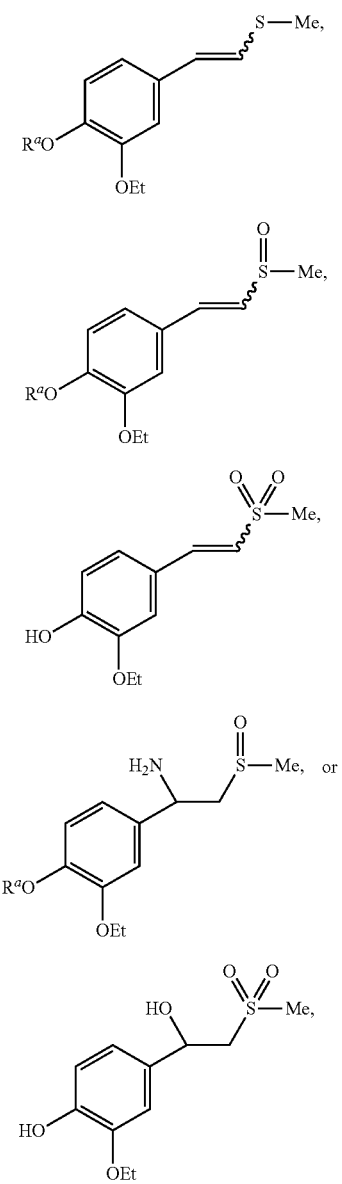

wherein $R^a$ is hydrogen or methyl, and the wavy lines indicate (E)- or (Z)-isomer or a mixture of (E)- and (Z)-isomers.

(29) The compound according to item (28), wherein the compound having formula (VII) and/or (VIII) is a substantially racemic compound, preferably is the racemic compound.

(30) The compound according to item (28) or (29), wherein $R^a$ is methyl.

(31) The compound according to any one of items (28) to (30), wherein the compound having any one of the formulae (IV), (V) or (VI) is the (E)-isomer.

(32) Use of the compound according to any one of items (28) to (31) for preparing apremilast or a pharmaceutically acceptable salt or solvate thereof.

(33) A process comprising the steps of:

(xa) providing a compound of formula (III)

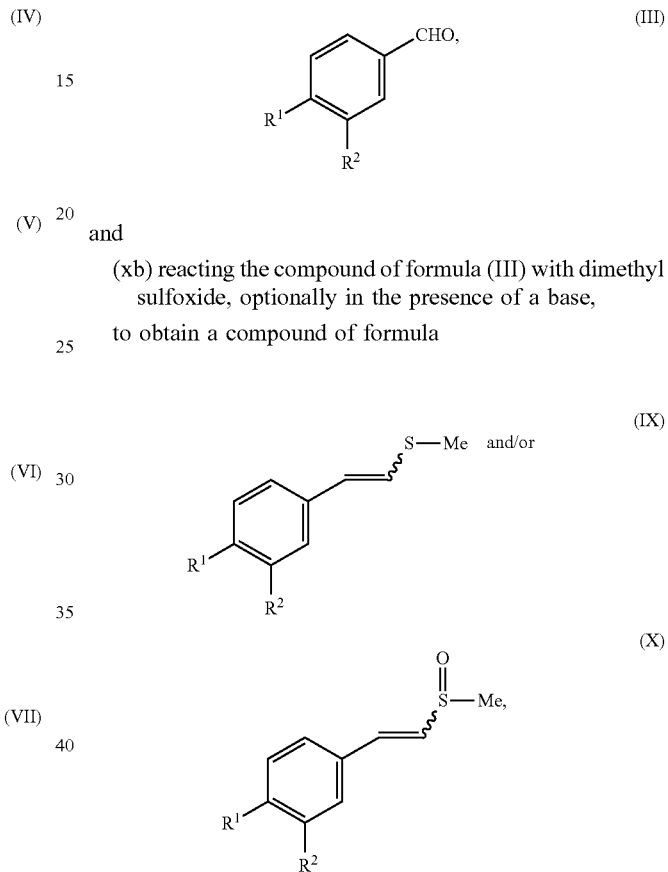

and (xb) reacting the compound of formula (III) with dimethyl sulfoxide, optionally in the presence of a base, to obtain a compound of formula wherein $R^1$ and $R^2$ are as defined in item (1), and the wavy lines indicate (E)- or (Z)-isomer or a mixture of (E)- and (Z)-isomers.

(34) The process according to item (33), wherein the compound of formula (IX) and/or (X) is the (E)-isomer.

(35) The process according to item (33) or (34), wherein substantially only compound of formula (IX) or substantially only compound of formula (X) is obtained.

(36) The process according to any one of items (33) to (35), wherein contacting according to step (xb) is carried out in the presence of a base, more preferably potassium tert-butoxide, KOH, $Et_3N$, $Cs_2CO_3$ or BuLi.

(37) The process according to any one of items (33) to (36), wherein dimethyl sulfoxide is used as reagent and the only solvent.

(38) The process according to any one of items (33) to (37), wherein further reaction(s) is (are) carried out to obtain a compound of formula (XI)

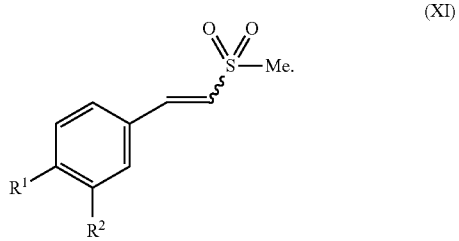

(39) The process according to item (38), wherein the compound of formula (XI) is the (E)-isomer.

(40) The process according to item (38) or (39), wherein the process is a one-pot process.

(41) The process according to any one of items (38) to (40), wherein formic acid and $H_2O_2$ are used for further reaction.

(42) A process comprising providing a compound of formula (II) as set forth in item (1) and contacting the compound of formula (II) with aqueous ammonia to obtain the compound of formula (I) as set forth in item (1), wherein $R^4$ and $R^5$ are hydrogen.

DETAILED DESCRIPTION

In the following, the present invention is described in more detail while referring to preferred embodiments and examples, which are presented however for illustrative purposes and shall not be construed to limit the invention in any way.

A first aspect of the invention is a process for preparing a compound of formula (I) or a salt or solvate thereof, wherein formula (I) is as follows:

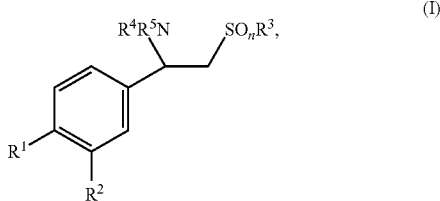

the process comprising the steps of providing a compound of formula (II)

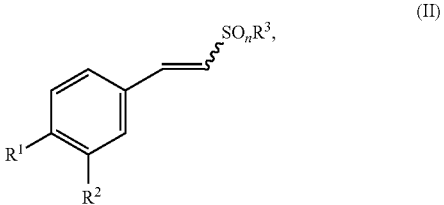

and contacting the compound of formula (II) with $R^4R^5NH$ or a conjugate base thereof or with $XYC=NH$ in a solvent, to obtain the compound of formula (I), wherein substituents are defined as follows:

$R^1$ and $R^2$ are each independently selected from the group consisting of hydrogen, hydroxy, halogen, nitro, cyano, —$CF_3$, substituted or unsubstituted $C_1$-$C_6$ alkyl, substituted or unsubstituted $C_3$-$C_6$ cycloalkyl, substituted or unsubstituted $C_1$-$C_6$ alkoxy, substituted or unsubstituted $C_3$-$C_6$ cycloalkoxy, substituted or unsubstituted $C_6$-$C_{10}$ aryl, and substituted or unsubstituted $C_7$-$C_{12}$ aralkyl;

$R^3$ represents substituted or unsubstituted $C_1$-$C_6$ alkyl, hydroxy, substituted or unsubstituted $C_6$-$C_{10}$ aryl, substituted or unsubstituted $C_7$-$C_{12}$ aralkyl, or —$NR^6R^7$, wherein $R^6$ and $R^7$ are each independently selected from the group consisting of hydrogen, substituted or unsubstituted $C_1$-$C_6$ alkyl, substituted or unsubstituted $C_6$-$C_{10}$ aryl, and substituted or unsubstituted $C_7$-$C_{12}$ aralkyl; $R^4$ and $R^5$ are each independently selected from the group consisting of hydrogen, hydroxy, and substituted or unsubstituted $C_1$-$C_4$ alkyl;

X and Y are each independently selected from phenyl and tert-butyl; and n is an integer selected from 0, 1 and 2. The wavy line indicates (E)- or (Z)-isomer or a mixture of (E)- and (Z)-isomers, that means it indicates trans and/or cis configuration.

It was advantageously found that the useful β-aminosulfonyl, β-aminosulfinyl and β-aminosulfanyl compounds of formula (I) can be obtained by aza-Michael addition. Starting from the alkene compounds of formula (II) the conjugate addition of amine and amine derivative reagents at the β-position can provide the compounds of formula (I) in a simple and robust chemical transformation.

The alkene compounds of formula (II) can be provided as the (E)-isomer, the (Z)-isomer, or a mixture thereof. It was advantageously found that in the process according to the invention no specific configuration is required. In a preferred embodiment the (E)-isomer is provided.

Furthermore, it was surprisingly and advantageously found that this synthesis can be carried out in a solvent comprising water. In a preferred embodiment a solvent is used that is substantially aqueous. The term "substantially aqueous" herein denotes that the solvent contains at least 50 wt % water, preferably at least 60 wt %, more preferably at least 70 wt %, even more preferably at least 80 wt %, still more preferably at least 90 wt % and yet more preferably at least 95 wt %. In a particularly preferred embodiment the solvent used is water. This means particularly preferably pure water without another solvent is used. However, trace amounts of inorganic salts or organic matter and other impurities may be contained in the water solvent as supplied. Most preferably purified water is used as the solvent, wherein distilled water, deionized water and water from microfiltration or ultrafiltration may be used. Using substantially aqueous solvent or even only water as solvent provides substantial benefits. Water is abundant and inexpensive and is an environmentally friendly reaction medium. Thus advantageously the use of polluting, toxic and volatile organic solvents can unexpectedly be reduced or even avoided.

In particular, using the reagent $R^4R^5NH$ as defined in item (1), having beneficial properties including favourably sufficient water solubility, the aza-Michael addition according to the invention can advantageously be carried out in aqueous solvent. Therefore, in a preferred embodiment the process is carried out by providing the reagent $R^4R^5NH$ as defined combined with using aqueous solvent, more preferably water, thus providing additional benefits. Advantageously the respective amino products can be obtained directly and additional step(s) of deprotection or cleaving of auxiliary groups can favourably and preferably be avoided.

Preferably the reaction is carried out at a temperature from 25° C. to 135° C., more preferably from 50° C. to 110° C., even more preferably from 60° C. to 100° C., still more preferably from 80° C. to 100° C., and in particular at around 80° C. When aqueous solvent is used or water is used as the solvent the reaction temperature is set at or below boiling temperature, particularly preferably from 80° C. to 100° C. According to an embodiment the conjugate addition is carried out in the presence of a catalyst, preferably an acid catalyst, more preferably boric acid catalyst. The acid catalyst can comprise Brønsted and/or Lewis acids. Suitable acid catalysts are known in the art.

The compounds of formula (I) have a chiral centre and can exist as optical isomers, i.e. the S enantiomer or the R enantiomer. Both the racemates of these isomers and the individual isomers themselves, and also diastereomers where two chiral centres exist, are within the scope of the present invention. Enantiomerically pure chiral compounds can be obtained by isolating or separating the enantiomers from the racemic compound using techniques, so-called chiral or optical resolution, known in the art. Examples include the use of chiral salts and of chiral chromatography, wherein derivatization and ultimately separation of racemic compounds is possible by forming pairs of diastereomers with optically pure reagents.

However, according to a preferred embodiment the compound of formula (I) is a substantially racemic compound, preferably is the racemic compound. The term "substantially racemic" denotes that the enantiomeric excess is less than 20%, preferably less than 10%, more preferably less than 5%. Particularly preferably there is no enantiomeric excess.

In the process according to the invention for obtaining the compound of formula (I) therefore preferably the use of asymmetric reactions and chiral auxiliaries is avoided. This means preferably the conjugate addition does not proceed in a stereoselective manner such that the compounds of formula (I) are substantially racemic, preferably racemic. This can be advantageous in several ways. For example, the use of a stoichiometric amount of chiral auxiliary, e.g. chiral amines, can be expensive. Moreover, when aiming to provide a particular enantiomer in high purity, an approach using a chiral auxiliary can lack efficiency of enantioselectivity such that additional steps are required to obtain sufficient optical purity, e.g. crystallizations and isolation. Furthermore, a deprotection or scission step cleaving the chiral auxiliary is necessary, which may require expensive reagents such as transition metals, e.g. Pd or Pt. Such cleaving of the chiral auxiliary may also lack efficiency and/or selectivity. Another disadvantage of the asymmetric approach is that specifically the (E)-isomer, or alternatively (Z)-isomer, of the alkene starting material has to be provided, which is a prerequisite for aiming at controlling the outcome of the stereoselective addition. Likewise, enantioselective processes based on asymmetric catalysis, e.g. asymmetric catalytic hydrogenation, also require the use of expensive materials, e.g. transition metals such as Rh or Ru and particular ligands, and can also be inefficient and inconvenient.

It was advantageously found that significant advantages can be obtained by preparing the compound of formula (I) in a substantially racemic, preferably racemic form. Mild reaction conditions can be used and there is no need for an additional cleavage step. Simple and inexpensive reagents can be used. Furthermore, the reaction does not require the provision of specifically the (E)-isomer or (Z)-isomer, which means that not only the (E)-isomer, or alternatively the (Z)-isomer can be used, but also a mixture of both. Therefore, preferably, the compound of formula (I) is prepared as a substantially racemic product, preferably as the racemic product. When using the compound of formula (I) as a precursor in further syntheses and if required, chiral resolution can economically and efficiently be used to provide or make use of the desired isomer in high purity. Optionally, racemization and consequent recycling of the undesired enantiomer can be carried out to provide the final compound, e.g. apremilast, in an overall even more efficient process.

In a preferred embodiment $R^4$ or $R^5$ represents hydrogen. In a further preferred embodiment ammonia is used as the amine reagent, even more preferably aqueous ammonia is used. The amine reagent may also comprise a conjugate base of the amino compound.

Alternatively, the product of formula (I) can be prepared using amino-group-introducing reagents selected from imines of the formula XYC=NH, wherein X and Y are each independently selected from phenyl and tert-butyl. The thereby obtained intermediate of formula (I'), preferably without intermediate purification or isolation,

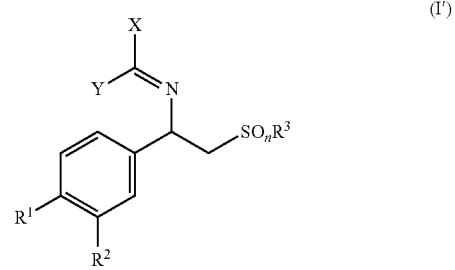

(I')

is routinely further transformed to the compound of formula I. In the case where $R^4$ and $R^5$ are hydrogen, the product can be prepared using acidic medium, for example using acidic medium in the step of isolating the product.

Preferred compounds exhibit the following substituents: $R^1$ is methoxy or hydroxy, preferably is methoxy, $R^2$ is ethoxy, and $R^3$ is methyl. A particularly preferred compound obtained in the process according to the present invention is 2-(3-ethoxy-4-methoxyphenyl)-1-(methanesulfonyl)-eth-2-ylamine, having formula (Ia)

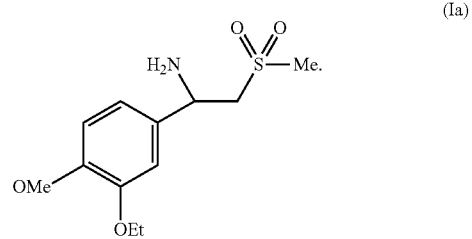 [SMILES: CCOc1cc(C(N)CS(C)(=O)=O)ccc1OC]

(Ia)

Further preferred obtainable compounds are 2-(3-ethoxy-4-methoxyphenyl)-1-(methanesulfinyl)-eth-2-ylamine and 2-(3-ethoxy-4-methoxyphenyl)-1-(methanesulfanyl)-eth-2-ylamine.

In the aza-Michael addition according to the invention an alkene compound having formula (IIa)

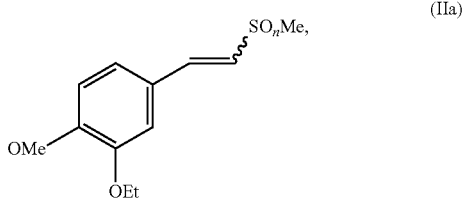

(IIa)

wherein n is an integer selected from 0, 1 and 2, is preferably used as a starting material. Preferably the compound of formula (IIa) is the (E)-isomer.

In an embodiment the compounds of formula (II) can be provided by a process that comprises providing a compound of formula (III)

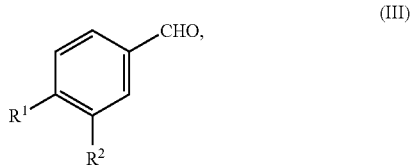

(III)

and contacting the compound of formula (III) with $R^8SO_mR^9$, optionally in the presence of a base, wherein $R^1$ and $R^2$ are as defined in item (1) above, $R^8$ and $R^9$ each independently correspond to $R^3$ as defined in item (1) above, and m is 1 or 2.

It was advantageously found that the α,β-unsaturated alkene compounds of formula (II) can be provided by a simple and robust condensation of the suitable benzaldehyde derivatives of formula (III) using the $R^8SO_mR^9$ reagent as defined. The transformation can proceed via adduct formation giving the β-hydroxy intermediate followed by dehydration elimination.

In a preferred embodiment the (E)-alkenes are obtained. Without wishing to be bound by theory, it is believed that usually the trans-substituted alkenes are preferably produced as the thermodynamically more stable alkenes. However, conditions may be chosen such that the (Z)-isomer, i.e. the cis-substituted alkenes, are obtained, e.g. by using a dehydration mechanism from a solid surface. Moreover, not being limited to the described embodiment, the compounds of formula (II) may be prepared by any suitable method, wherein the prepared compounds of formula (II) can be provided as the (E)-isomer, the (Z)-isomer, or a mixture thereof. Favourably (E)-isomer and/or (Z)-isomer can be used as starting material in the aza-Michael addition according to the present invention.

Preferably $Me_2SO_2$ and dimethyl sulfoxide (DMSO) are used in the condensation reaction with the benzaldehyde derivatives. $R^8SO_mR^9$, preferably $Me_2SO_2$ and DMSO, can be further activated using a base. Suitable bases are known in the art, for example potassium tert-butoxide, KOH, $Et_3N$, $Cs_2CO_3$ or BuLi may be used.

The β-hydroxy sulfonyl, sulfinyl and sulfanyl compounds as intermediates of the condensation reaction may be isolated. That is the β-hydroxy adducts may be separated from the reaction mixture before the dehydration elimination yielding the α,β-unsaturated compounds of formula (II) occurs. The β-hydroxy intermediates may be used for later and also different transformations. Thus in the present invention the respective β-hydroxy compounds can be provided as starting materials for various syntheses.

Use of DMSO and $Me_2SO_2$ provides the respective methylsulfonyl, methylsulfinyl and methylsulfanyl compounds. This is particularly favourable for further synthesis to obtain apremilast. Specifically, using $Me_2SO_2$ the methylsulfonyl compounds can be directly obtained. When DMSO is used either the methylsulfanyl compounds can be obtained by reductive condensation or the methylsulfinyl compounds can be obtained. This way various suitable intermediate compounds can be obtained, wherein n as defined in item (1) above can be 0, 1 or 2. These may be useful for different further syntheses.

If desired, for example in the preparation of apremilast, the methylsulfinyl and methylsulfanyl compounds can be further converted to the corresponding methylsulfonyl compounds. Various oxidation reactions are known in the art. For example, after the condensation formic acid and $H_2O_2$ can be added to the reaction mixture such that the methylsulfonyl compounds are formed.

In a preferred embodiment the benzaldehyde derivatives of formula (III) are used, wherein wherein $R^1$ is methoxy or hydroxy, and $R^2$ is ethoxy. Furthermore, $R^1$ and $R^2$ can also both be hydroxy. In a case where a substituent on the phenyl ring is hydroxy, in the 3-position and/or 4-position, preferably in the 4-position, the hydroxy group can be suitably transformed at a later stage if desired, possibly in the final step of the synthesis. For example, $Me_2SO_4$ may be used such that the hydroxy group is converted to the methoxy group.

In a particularly preferred embodiment 3-ethoxy-4-methoxy-benzaldehyde, having formula (IIIa)

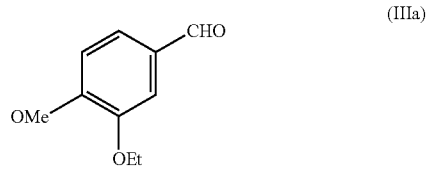 [SMILES: CCOc1cc(C=O)ccc1OC]

(IIIa)

is used as the starting material for the condensation. This compound is especially advantageous in view of a short and simple synthesis of apremilast.

The compounds of formula (I) can be useful precursors and intermediates for further chemical transformations and synthesis. These include, but are not limited to, syntheses of further β-aminosulfone compounds, in particular apremilast and related derivatives.

In another aspect of the present invention a process is provided for preparing apremilast or a pharmaceutically acceptable salt or solvate thereof, comprising carrying out the process according to the invention to obtain the compound of formula (I), and subsequently carrying out further synthetic step(s) to obtain apremilast.

In the present invention it was found that especially advantageous and preferable intermediates for preparing apremilast are compounds, wherein $R^1$ is methoxy or hydroxy, $R^2$ is ethoxy, and $R^3$ is methyl. Furthermore, preferably $R^4$ or $R^5$ represents hydrogen, more preferably $R^4$ and $R^5$ each represent hydrogen. Particularly preferably $R^1$ is methoxy, and $R^4$ and $R^5$ are each hydrogen.

A particularly useful intermediate in the synthesis of apremilast was found to be the β-aminosulfone compound 2-(3-ethoxy-4-methoxyphenyl)-1-(methanesulfonyl)-eth-2-ylamine, having formula (Ia)

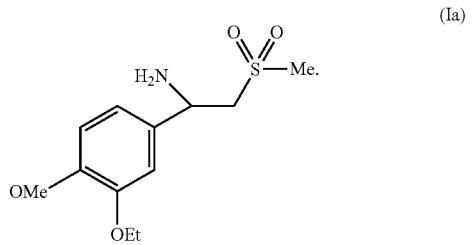 [SMILES: CCOc1cc(C(N)CS(C)(=O)=O)ccc1OC]
(Ia)

This compound can be prepared according to the invention in an advantageously short and simple process based on aza-Michael conjugate addition, preferably in aqueous medium. This means compound of formula (Ia) can advantageously be provided by the conjugate addition of aqueous ammonia reagent to the α,β-unsaturated bond of the sulfonyl compound according to formula (IIa).

Using compound of formula (I), preferably compound of formula (Ia), synthetic step(s) to obtain apremilast is (are) facile. For example, referring to WO 00/25777 A1 and WO 03/080049 A1, the racemic product of formula (Ia) can be optically resolved using chiral compounds such as chiral amino acids, e.g. N-acetyl-L-leucine. Apremilast can then for example be obtained in a synthesis using 3-acetamidophthalic anhydride and the chiral amino acid salt of the (S) enantiomer of the β-aminosulfone compound of formula (Ia), e.g. carried out in acetic acid. Optionally, racemization and consequent recycling of the undesired (R) enantiomer of the β-aminosulfone compound of formula (Ia) can be carried out to provide apremilast in an overall even more efficient process.

The process to prepare apremilast preferably comprises chiral resolution or chiral enrichment. When using the sulfinyl or sulfanyl intermediates suitable oxidations to obtain the sulfonyl group can be carried out. In the Michael conjugate addition preferably ammonia is used, e.g. aqueous ammonia.

Another aspect of the invention is a process for preparing a pharmaceutical composition comprising apremilast or a pharmaceutically acceptable salt or solvate thereof, the process comprising the steps of carrying out the process of the invention to obtain apremilast or a pharmaceutically acceptable salt or solvate thereof, and mixing apremilast or a pharmaceutically acceptable salt or solvate thereof obtained according to the invention, optionally with another active pharmaceutical ingredient, with a pharmaceutically acceptable excipient, carrier and/or diluent.

In particular, apremilast or a pharmaceutically acceptable salt or solvate thereof is admixed with at least one suitable pharmaceutically acceptable excipient. Pharmaceutically acceptable excipients may be selected from the group consisting of diluents, carriers, binders, disintegrating agents, stabilizing agents, preservatives, lubricants, surfactants, fragrances, flavouring agents, sweeteners and other excipients known in the field of the pharmaceutical technology. For example, suitable excipients may be selected from the group consisting of lactose, microcrystalline cellulose, cellulose derivatives, such as hydroxypropylcellulose, polyacrylates, calcium carbonate, starch, colloidal silicone dioxide, sodium starch glycolate, croscarmellose sodium, talc, magnesium stearate, polyvinylpyrrolidone, polyethylene glycol and other excipients known in the field of the pharmaceutical technology.

In another aspect of the invention a compound having any one of the following formulae:

(IV)

(V)

(VI)

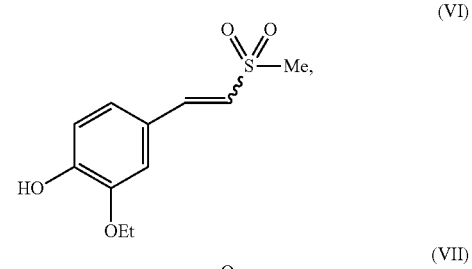
(VII)

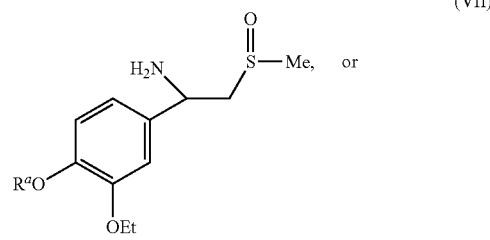
(VIII)

is provided, wherein $R^a$ is hydrogen or methyl, and the wavy lines indicate (E)- or (Z)-isomer or a mixture of (E)- and (Z)-isomers. Preferably the compound having formula (VII) and/or (VIII) is a substantially racemic compound, more preferably is the racemic compound. Preferably, $R^a$ is methyl. If desired, hydroxyl group on the phenyl ring can be suitably converted to the methoxy group.

Compounds (IV), (V), (VI), (VII) and (VIII) are respectively useful sulfonyl, sulfinyl and sulfanyl compounds which can be advantageously used as precursors in chemical transformations and synthetic processes. In particular, these compounds can be favourably used for preparing apremilast or a pharmaceutically acceptable salt or solvate thereof as well as related derivatives of apremilast. Preferably the compounds of formulae (IV), (V) and (VI) are the (E)-isomers.

Another aspect of the invention is a process which comprises providing a compound of formula (III)

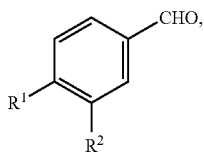

(III)

and
reacting the compound of formula (III) with dimethyl sulfoxide (DMSO), optionally in the presence of a base, to obtain a compound of formula

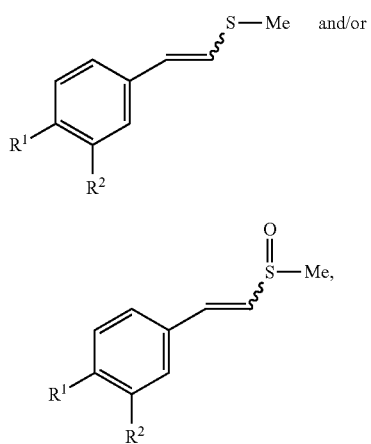

(IX) and/or (X)

wherein R¹ and R² are as defined in item (1), and the wavy lines indicate (E)- or (Z)-isomer or a mixture of (E)- and (Z)-isomers.

Preferably the compound of formula (IX) and/or (X) is the (E)-isomer. Advantageously DMSO can be used simultaneously as reagent as well as solvent. Preferably DMSO is the only solvent used in the preparation of compound of formula (IX) and/or (X) from compound (III). Preferably DMSO can be further activated by base. Suitable bases are known in the art, for example potassium tert-butoxide, KOH, Et₃N, Cs₂CO₃ or BuLi may be used.

Advantageously conditions can be chosen such that either substantially only compound of formula (IX), preferably only compound of formula (IX), or substantially only compound of formula (X), preferably only compound of formula (X), is obtained. For example, the unsaturated sulfide product may be prepared by reductive condensation of the benzaldehyde derivative in DMSO, e.g. in the presence of potassium tert-butoxide at a suitable temperature, for example at around 100° C. On the other hand, the unsaturated sulfoxide product may be prepared in DMSO for example in the presence of Cs₂CO₃ or KOH at a suitable temperature, e.g. at around 60° C. However, also mixtures of compounds of formulae (IX) and (X) can be provided. These compounds are useful intermediates and precursors and may be used in further synthesis.

The transformation from the benzaldehyde derivatives to the respective alkenes can proceed via adduct formation giving the β-hydroxy intermediate followed by dehydration elimination. It can be possible to separate the β-hydroxy adducts from the reaction mixture before the dehydration elimination yielding the α,β-unsaturated compounds, wherein the β-hydroxy intermediates may be used for later and also different transformations.

In a preferred embodiment the unsaturated sulfide compound of formula (IX) and/or the unsaturated sulfoxide compound of formula (X) is (are) further reacted to obtain a compound of formula (XI)

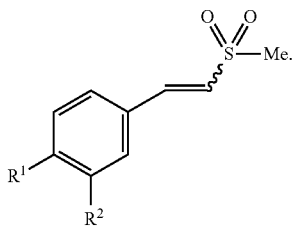

(XI)

Preferably the compound of formula (XI) is the (E)-isomer. Advantageously and preferably the compound of formula (XI) can be prepared from compound of formula (III) in a one-pot process. This provides significant advantages, for example by avoiding the need for intermediate purification and/or isolation. The sulfide derivatives, the sulfoxide derivatives, and mixtures thereof can be converted to the sulfone compounds of formula (XI) by suitable oxidation reactions known in the art. Preferably formic acid and H₂O₂ are used. Therefore, advantageously and preferably this process can make use of simple and inexpensive reagents such as DMSO, H₂O₂, formic acid and inexpensive bases, which are preferably mild bases.

The compounds of formula (XI) are useful intermediates which may be used in further syntheses. In a particularly preferred embodiment R¹ is methoxy or hydroxy, preferably methoxy, and R² is ethoxy. In this case particularly advantageous precursors for the synthesis of apremilast are provided.

While condensation of aldehydes as well as aza-Michael addition have generally been known, referring to e.g. the descriptions in Ma et al., Tetrahedron Letters, vol. 43, pp. 8511-8513, 2002 and Wada et al., J. Med. Chem., vol. 45, pp. 219-232, 2002, it was surprisingly found that such reactions can beneficially be applied, and advantageously and preferably be combined, in the specific present synthetic contexts, thus unexpectedly providing significant benefits and advantages. In particular, surprisingly simple amine reagents as set forth in item (1), and in addition simple condensations with DMSO or Me₂SO₂, can be used, while providing very efficient and selective processes.

Using aza-Michael addition processes according to the invention, and furthermore using the condensation processes on the benzaldehyde derivatives according to the invention, simple, short and robust processes are provided to directly form and provide the useful intermediate compounds according to the invention. Moreover, unexpectedly the use of aqueous solvent in the present aza-Michael addition is possible, which surprisingly provides further additional advantages.

While advantageously additional protection/deprotection steps can be avoided in the processes according to the invention, use of protecting groups is however possible. Suitable uses and choices of protecting groups and the respective reaction conditions for protection and deprotection are known in the art, referring to e.g. the description in P. G. M. Wuts and T. W. Greene, "Greene's Protective Groups in Organic Synthesis", 4th Edition, Wiley, 2006.

The present invention advantageously provides short and simple processes for preparing β-amino sulfone, sulfoxide and sulfide intermediates useful for the preparation of sulfone group containing isoindoline-based compounds, in particular apremilast. Starting from benzaldehyde derivatives and based on aza-Michael conjugate addition the intermediates can be obtained via a short and simple 2-step-process. The overall synthetic process to obtain apremilast according to the invention provides simple and robust chemical transformations. Simple and commercially available reagents, and optionally catalysts, are used, and the intermediates may be formed directly without the need for additional protection/deprotection steps. Hazardous, toxic and expensive chemicals can favourably be avoided. Moreover, in the aza-Michael conjugate addition step, instead of polluting, toxic and volatile organic solvents, water can advantageously be used which is an abundant and eco-friendly reaction medium. In addition, there is no need for cumbersome preparatory equipment or techniques. Overall, the present invention thus provides cost-effective, environmentally friendly and industrially suitable synthetic processes.

EXAMPLES

The following examples are merely illustrative of the present invention and they should not be considered as limiting the scope of the invention in any way. The examples and modifications or other equivalents thereof will become apparent to those versed in the art in the light of the present entire disclosure.

Example 1

Example 1a: Reductive Condensation of 3-ethoxy-4-methoxy-benzaldehyde in DMSO in the presence of KOBut to form unsaturated (E)-(3-ethoxy-4-methylstryl)(methyl)-sulfane

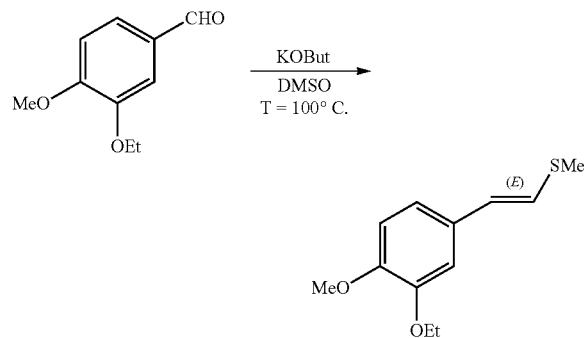

Into a 10 mL test tube equipped with magnetic stir bar was placed KOBut (1.5 mmol, 168 mg, 1.5 equiv. according to starting material), it was dissolved in anhydrous DMSO (2.5 mL) and reaction mixture was stirred for 10 minutes. Afterwards the starting material 3-ethoxy-4-methoxy-benzaldehyde (1 mmol, 180 mg) was added in two portions and such reaction mixture was vigorously stirred at 100° C. The reaction was followed by TLC and after the completion of the reaction, reaction system was cooled down to room temperature, diluted with water and extracted with EtOAc (50 mL). Organic phases were washed with brine, dried over anhydrous Na$_2$SO$_4$ and solvent was evaporated under reduced pressure. The obtained crude product was purified with flash chromatography (SiO$_2$, n-hexane: EtOAc) and solid material (182 mg, 81%) was analyzed and confirmed using GC-MS (224 m/z) and NMR spectroscopy.

$^1$H NMR (500 MHz, CDCl$_3$) δ 6.95-6.70 (m, 3ArH), 6.60 (d, J=15.4 Hz, 1H), 6.35 (d, J=15.4 Hz, 1H), 4.15 (q, 2H), 3.85 (s, 3H), 2.40 (s, 3H), 1.45 (t, 3H);

$^{13}$C NMR (125 MHz, CDCl$_3$, ppm) δ 148.4, 148.3, 127.1, 125.0, 118.9, 112.1, 111.7, 109.6, 64.3, 56.1, 29.7, 14.9.

Example 1b: Synthesis of Unsaturated Sulfone (E)-2-ethoxy-1-methyl-4-(2-(methylsulfonyl)-vinyl)benzene

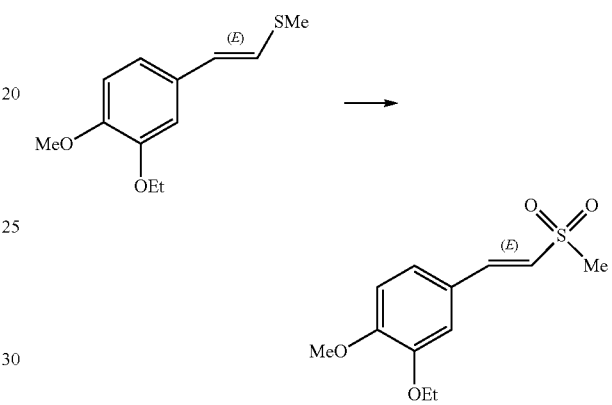

Into a 50 mL vessel equipped with magnetic stir bar was placed starting material (E)-(3-ethoxy-4-methylstryl)(methyl)sulfane (0.45 mmol, 100 mg) and formic acid was added to get clear solution. Reaction system was cooled down to 0° C. where 30% aq. H$_2$O$_2$ was slowly added and reaction mixture was vigorously stirred at 27° C. till TLC showed final consumption of starting material. The reaction system was diluted with water, neutralized with saturated solution of NaHCO$_3$ and then extracted with CH$_2$Cl$_2$. Organic phases were washed with brine, dried over anhydrous Na$_2$SO$_4$ and solvent was evaporated under reduced pressure where solid orange material was obtained as a crude product. Crude product was recrystallized from MTBE (82 mg, 71% yield) and analyzed using GC-MS (256 m/z) and $^1$H NMR spectroscopy.

$^1$H NMR (500 MHz, CDCl$_3$) δ 7.50 (d, J=15.4 Hz, 1H), 7.10 (dd, J=8.4 Hz, J=2.0 Hz, ArH), 7.00 (d, J=2 Hz, ArH), 6.90 (d, J=8.4 Hz, ArH), 6.80 (d, J=15.4 Hz, 1H), 4.13 (q, J=7.0 Hz, 2H), 3.90 (s, 3H), 3.05 (s, 3H), 1.50 (t, J=7 Hz, 3H).

Example 2: Synthesis of Unsaturated Sulfoxide (E)-2-ethoxy-1-methyl-4-(2-(methylsulfinyl)-vinyl) benzene in the presence of Cs$_2$CO$_3$

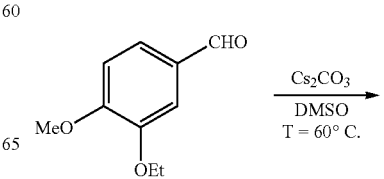

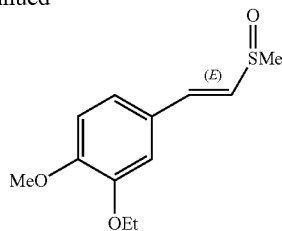

Into a 10 mL test tube equipped with magnetic stir bar was placed Cs$_2$CO$_3$ (1.5 equiv. according to starting material), it was suspended in anhydrous DMSO (3 mL) and reaction mixture was stirred for 15 minutes at room temperature. Afterwards the starting material 3-ethoxy-4-methoxy-benzaldehyde (1 mmol, 180 mg) was added in two portions and such reaction mixture was vigorously stirred at 60° C. for two days. The reaction system was cooled down to room temperature, diluted with water and extracted with EtOAc (50 mL). Organic phases were washed with brine, dried over anhydrous Na$_2$SO$_4$ and solvent was evaporated under reduced pressure. The obtained crude product was purified with flash chromatography (SiO$_2$, n-hexane EtOAc) and solid material (160 mg, 62%) was analyzed and confirmed using GC-MS (256 m/z) and NMR spectroscopy.

$^1$H NMR (500 MHz, CDCl$_3$) δ 7.16 (d, J=15.5 Hz, 1H), 7.00 (dd, J=8.3 Hz, J=2.1 Hz, ArH), 6.99 (d, J=2 Hz, ArH), 6.86 (d, J=8.3 Hz, ArH), 6.70 (d, J=15.5 Hz, 1H), 4.15 (q, J 7.1 Hz, 2H), 3.85 (s, 3H), 2.70 (s, 3H), 1.45 (t, J=7.1 Hz, 3H);

$^{13}$C NMR (125 MHz, CDCl$_3$, ppm) δ 150.8, 148.4, 136.8, 129.6, 121.3, 111.7, 110.9, 64.3, 56.1, 41.0, 14.7.

Example 3: Synthesis of Unsaturated Sulfoxide (E)-2-ethoxy-1-methyl-4-(2-(methylsulfinyl)-vinyl)benzene Followed by Oxidation to (E)-2-ethoxy-1-methyl-4-(2-(methyl-sulfonyl)vinyl)benzene

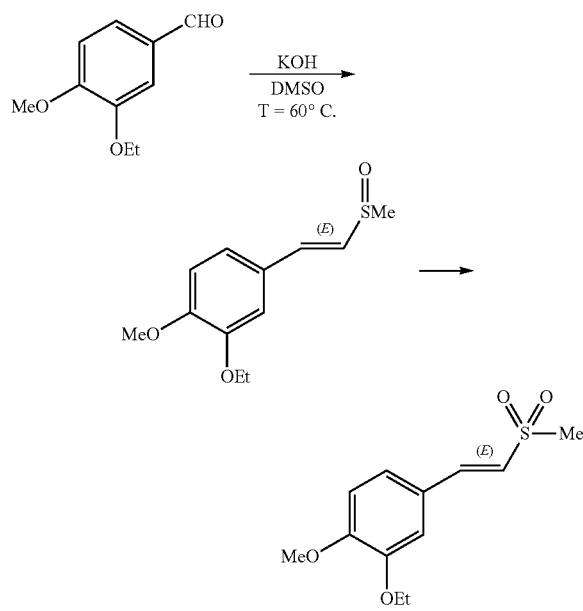

Into a 100 mL glass reactor equipped with magnetic stir bar was placed KOH (1 equiv. according to starting material), it was suspended in anhydrous DMSO (30 mL) and reaction mixture was stirred for 15 minutes at room temperature. Afterwards the starting material 3-ethoxy-4-methoxy-benzaldehyde (27 mmol, 4.87 g) was added in two portions and such reaction mixture was vigorously stirred at 60° C. for 3 hours. The reaction system was cooled down to room temperature, diluted with water and extracted with EtOAc (50 mL). Organic phases were washed with brine, dried over anhydrous Na$_2$SO$_4$ and solvent was evaporated under reduced pressure. The obtained crude product was dissolved in CH$_2$Cl$_2$ (22 mL) and formic acid (1.1 mL) was added. Afterwards the reaction system was cooled down to 0° C. where 30% aqueous H$_2$O$_2$ was slowly added and reaction system was stirred at 27° C. overnight. The reaction system was diluted with water, neutralized with saturated solution of NaHCO$_3$ and then extracted with CH$_2$Cl$_2$. Organic phases were washed with brine, dried over anhydrous Na$_2$SO$_4$ and solvent was evaporated under reduced pressure where solid orange material was obtained as a crude product. Crude product was recrystallized from MTBE (4.93 g, 69% yield) and analyzed using GC-MS (272 m/z) and $^1$H NMR spectroscopy.

$^1$H NMR (500 MHz, CDCl$_3$) δ 7.50 (d, J=15.4 Hz, 1H), 7.10 (dd, J=8.4 Hz, J=2.0 Hz, ArH), 7.00 (d, J=2 Hz, ArH), 6.90 (d, J=8.4 Hz, ArH), 6.80 (d, J=15.4 Hz, 1H), 4.13 (q, J=7.0 Hz, 2H), 3.90 (s, 3H), 3.05 (s, 3H), 1.50 (t, J=7 Hz, 3H).

Example 4: Direct Synthesis of (E)-2-ethoxy-1-methyl-4-(2-(methylsulfonyl)vinyl)benzene

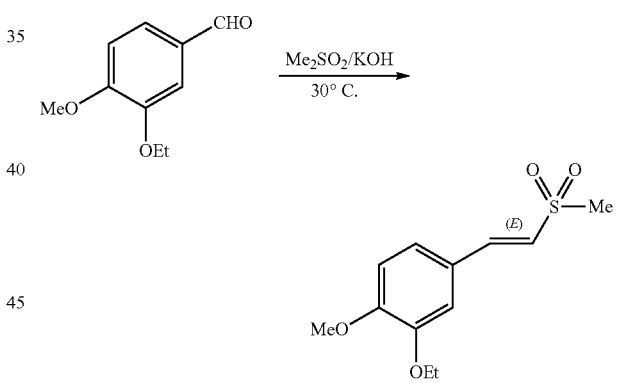

Into a 100 mL glass reactor equipped with magnetic stir bar were placed dimethylsulfone (2.5 equiv. according to starting material), KOH (1.5 equiv.) and were suspended in DMF (50 mL) Reaction mixture was stirred for 15 minutes at room temperature. Afterwards the starting material 3-ethoxy-4-methoxy-benzaldehyde (27 mmol, 4.87 g) was added in two portions and such reaction mixture was vigorously stirred at 60° C. for 2 hours. The reaction system was cooled down to room temperature, diluted with saturated aqueous solution of NH$_4$Cl and extracted with EtOAc (2×60 mL). Organic phases were washed with brine, dried over anhydrous Na$_2$SO$_4$ and solvent was evaporated under reduced pressure. The obtained crude product was purified with column chromatography (SiO$_2$, n-hexane: EtOAc gradient elution) to afford yellowish solid material (4.2 g, 59% yield) which was analyzed and confirmed using NMR spectroscopy. $^1$H NMR (500 MHz, CDCl$_3$) δ 7.50 (d, J=15.4 Hz, 1H), 7.10 (dd, J=8.4 Hz, J=2.0 Hz, ArH), 7.00 (d, J=2

Hz, ArH), 6.90 (d, J=8.4 Hz, ArH), 6.80 (d, J=15.4 Hz, 1H), 4.13 (q, J=7.0 Hz, 2H), 3.90 (s, 3H), 3.05 (s, 3H), 1.50 (t, J=7 Hz, 3H);

$^{13}$C NMR (125 MHz, CDCl₃, ppm) δ 152.2, 148.6, 144.0, 124.7, 123.4, 111.2, 64.4, 55.9, 43.5, 14.7.

Example 5: Synthesis of 2-ethoxy-4(1-hydroxy-2-(methylsulfonyl)ethyl)phenol

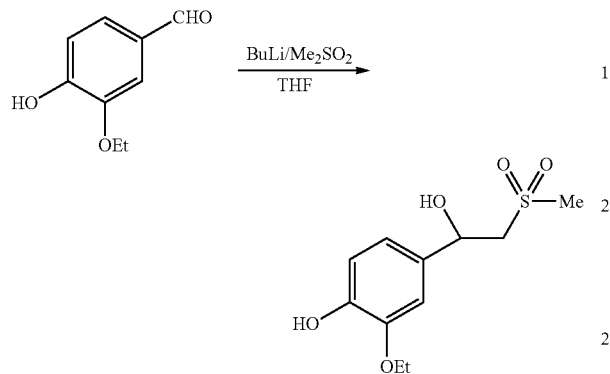

Into a 50 mL glass flask equipped with magnetic stir bar was placed dimethylsulfone (1 equiv. according to starting material) and was dissolved in THF. The reaction system was cooled down to −70° C. where 2.7 M BuLi in n-hexane (2 equiv.; 0.74 mL) was slowly added and reaction mixture was stirred at low temperature for 1 hour. Afterwards the THF solution of starting material 3-ethoxy-4-hydroxy-benzaldehyde (1 mmol) was added and such reaction mixture was vigorously stirred at 27° C. for 3 hours and then at 50° C. overnight. The reaction system was cooled down to room temperature, quenched with saturated aqueous solution of NH₄Cl and extracted with EtOAc (2×60 mL). Organic phases were washed with brine, dried over anhydrous Na₂SO₄ and solvent was evaporated under reduced pressure. The obtained crude product was purified with column chromatography (SiO₂, n-hexane: EtOAc gradient elution) to afford yellowish s material (140 mg, 53% yield) which was analyzed and confirmed using HPLC-MS and $^1$H NMR spectroscopy.

$^1$H NMR (500 MHz, CDCl₃) δ 6.95 (m, 3ArH), 5.35 (m, 1H), 4.15 (q, J=7.0 Hz, 2H), 3.45 (dd, J=10.3 Hz, J=14.7 Hz, 1H), 3.15 (m, 1H), 3.10 (s, 3H), 1.45 (t, J=7.0 Hz, 3H).

Example 6: Synthesis of (E)-2-ethoxy-4-(2-(methylsulfonyl)vinyl)phenol

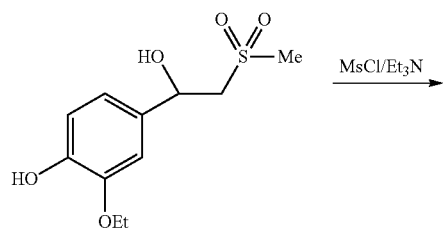

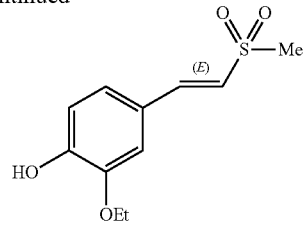

Into a 50 mL glass flask equipped with magnetic stir bar was placed 2-ethoxy-4-(1-hydroxy-2-(methylsulfonyl)ethyl)phenol (1 mmol) and was dissolved in CH₂Cl₂. The reaction system was cooled down to 0° C. where Et₃N (2 equiv.) was added and reaction mixture was stirred at low temperature for 15 minutes. Afterwards methanesulfonylchloride (1.5 equiv.) was slowly dropped into solution and such reaction mixture was vigorously stirred at room temperature overnight. The reaction system was quenched with saturated aqueous solution of NH₄Cl and phases were separated. Organic phases were washed with brine, dried over anhydrous Na₂SO₄ and solvent was evaporated under reduced pressure. The obtained crude product was analysed and confirmed with HPLC-MS (242 m/z).

Example 7: Synthesis of (E)-2-ethoxy-4-(2-(methylsulfonyl)vinyl)phenol

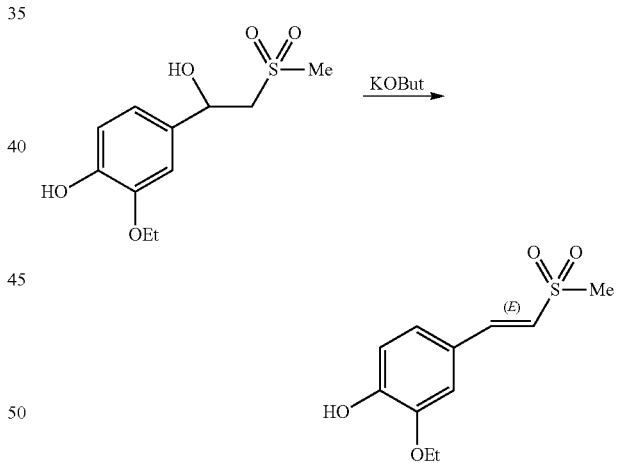

Into a 50 mL glass flask equipped with magnetic stir bar was placed 2-ethoxy-4-(1-hydroxy-2-(methylsulfonyl)ethyl)phenol (1 mmol) and was dissolved in DMF. Afterwards KOBut (1 equiv.) was added into solution and reaction mixture was vigorously stirred at 60° C. and reaction was followed by TLC. The reaction system was diluted with water, pH was adjusted to 3.5 with 1M aq. HCl and extracted with EtOAc. Organic phases were washed with brine, dried over anhydrous Na₂SO₄ and solvent was evaporated under reduced pressure. The obtained crude product was analysed and confirmed with HPLC-MS (242 m/z).

Example 8: Direct Synthesis of 1-(3-ethoxy-4-methylphenyl)-2-(methylsulfonyl)ethanamine in Aqueous Medium in the Presence of Boric Acid as Catalyst

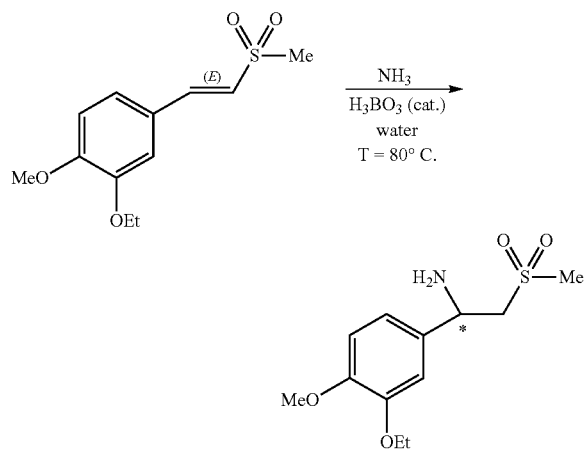

Into a 50 mL glass tube equipped with magnetic stir bar was placed boric acid (30 mol % according to starting material), was dissolved in water (1 mL) and stirred for 15 minutes at 50° C. Afterwards the starting material (E)-2-ethoxy-1-methyl-4-(2-(methylsulfonyl)vinyl)benzene (1 mmol) was added and such heterogeneous reaction system was vigorously stirred (900 rpm) at 60° C. for 10 minutes, where 28-32 wt % aqueous ammonia solution was added (10 mL). The homogenous reaction system was vigorously stirred at 80° C. in closed glass tube for 3 days. The reaction system was cooled down to room temperature and extracted with $CH_2Cl_2$ (2×30 mL). Organic phases were washed with water, dried over anhydrous $Na_2SO_4$ and solvent was evaporated under reduced pressure. The obtained solid product (205 mg, 75% yield) was characterized with GC-MS (273 m/z) and NMR spectroscopy.

$^1$H NMR (500 MHz, $CDCl_3$) δ 6.95-6.80 (m, 3ArH), 4.60 (dd, J=9.5 Hz, J=3.2 Hz, 1H), 4.15 (q, J=7.05 Hz, 2H), 3.80 (s, 3H), 3.33 (dd, J=9.5 Hz, J=14.0 Hz, 1H), 3.23 (dd, J=14.0 Hz, J=3.2 Hz, 1H), 2.90 (s, 3H), 1.85 (bs, NH), 1.45 (t, J=7.05 Hz, 3H);

$^{13}$C NMR (125 MHz, $CDCl_3$, ppm) δ 148.9, 135.5, 123.3, 111.5, 110.5, 64.3, 63.1, 58.8, 58.5, 55.9, 50.9, 43.4, 14.7.

Example 9: Direct Synthesis of 1-(3-ethoxy-4-methylphenyl)-2-(methylsulfonyl)ethanamine in Pure Aqueous Medium

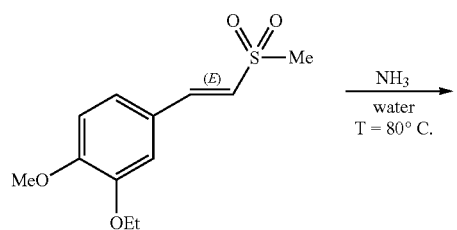

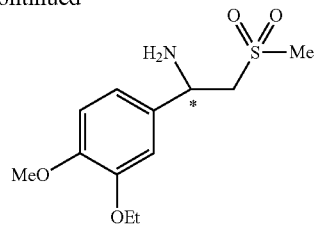

Into a 10 mL glass test tube equipped with magnetic stir bar was placed the starting material (E)-2-ethoxy-1-methyl-4-(2-(methylsulfonyl)vinyl)benzene (1 mmol) and was suspended 1 mL of water. Afterwards 28-32 wt % aqueous ammonia solution was added (10 mL) and homogenous reaction mixture was vigorously stirred at 80-100° C. in closed glass tube overnight. The reaction system was cooled down to room temperature and extracted with $CH_2Cl_2$ (2×30 mL). Organic phases were washed with water, dried over anhydrous $Na_2SO_4$ and solvent was evaporated under reduced pressure. The obtained solid product (190 mg, 69% Yield) was characterized with GC-MS (273 m/z) and NMR spectroscopy.

The invention claimed is:

1. A process for preparing a β-aminosulfone compound of formula (I)

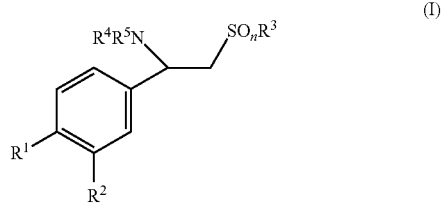

or a salt thereof, the process comprising the steps of:
(a) providing a compound of formula (II)

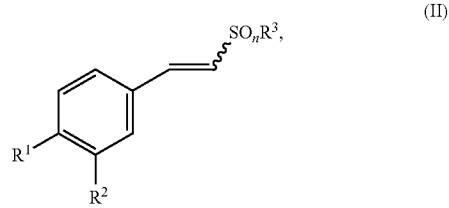

and
(b) contacting the compound of formula (II) with $R^4R^5NH$ or a conjugate base thereof or with XYC=NH in a solvent,
to obtain the compound of formula (I),
wherein $R^1$ and $R^2$ are each independently selected from the group consisting of hydrogen, hydroxy, halogen, nitro, cyano, —$CF_3$, substituted or unsubstituted $C_1$-$C_6$ alkyl, substituted or unsubstituted $C_3$-$C_6$ cycloalkyl, substituted or unsubstituted $C_1$-$C_6$ alkoxy, substituted or unsubstituted $C_3$-$C_6$ cycloalkoxy, substituted or unsubstituted $C_6$-$C_{10}$ aryl, and substituted or unsubstituted $C_7$-$C_{12}$ aralkyl;
$R^3$ represents substituted or unsubstituted $C_1$-$C_6$ alkyl, hydroxy, substituted or unsubstituted $C_6$-$C_{10}$ aryl, substituted or unsubstituted $C_7$-$C_{12}$ aralkyl, or —$NR^6R^7$, wherein $R^6$ and $R^7$ are each independently selected from the group consisting of hydrogen, substituted or unsubstituted $C_1$-$C_6$ alkyl, substituted or unsubstituted $C_6$-$C_{10}$ aryl, and substituted or unsubstituted $C_7$-$C_{12}$ aralkyl;

$R^4$ and $R^5$ are each independently selected from the group consisting of hydrogen, hydroxy, and substituted or unsubstituted $C_1$-$C_4$ alkyl;

X and Y are each independently selected from phenyl and tert-butyl;

n is an integer selected from 0, 1 and 2;

and the wavy line indicates (E)- or (Z)-isomer or a mixture of (E)- and (Z)-isomers.

2. The process according to claim 1, wherein the solvent comprises water.

3. The process according to claim 1, wherein the compound of formula (I) is a substantially racemic compound.

4. The process according to claim 1, wherein $R^1$ is methoxy or hydroxy, $R^2$ is ethoxy, and $R^3$ is methyl.

5. The process according to claim 1, wherein $R^4$ or $R^5$ represents hydrogen.

6. The process according to claim 1, wherein step (b) is carried out in the presence of a catalyst.

7. The process according to claim 1, wherein step (a) comprises:

(i) providing a compound of formula (III)

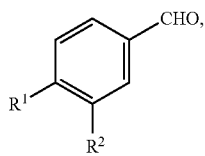

(III)

and (ii) contacting the compound of formula (III) with $R^8SO_mR^9$, optionally in the presence of a base, wherein $R^8$ and $R^9$ each independently correspond to $R^3$, and m is 1 or 2.

8. The process according to claim 7, wherein $R^8$ and $R^9$ each represent methyl.

9. A process for preparing apremilast or a pharmaceutically acceptable salt thereof, comprising:

(aa) preparing a compound of formula (I) according to the process of claim 1, and (bb) subsequently optically resolving the compound of formula (I) into its (S) and (R) enantiomers and reacting the (S) enantiomer with 3-acetamidophtalic anhydride to obtain apremilast.

10. A process for preparing a pharmaceutical composition comprising apremilast or a pharmaceutically acceptable salt thereof, the process comprising the steps of carrying out the process according to claim 9 to obtain apremilast or a pharmaceutically acceptable salt thereof, and mixing said obtained apremilast or a pharmaceutically acceptable salt thereof, optionally with another active pharmaceutical ingredient, with a pharmaceutically acceptable excipient, carrier and/or diluent.

* * * * *